United States Patent
Blankenbecler (10) Patent No.: US 7,963,902 B2
(45) Date of Patent: Jun. 21, 2011

(54) COMPUTER PRESCRIBED TREATMENT TO REDUCED DAMAGE FROM RADIATION THERAPY AND CHEMOTHERAPY

(75) Inventor: Richard Blankenbecler, Las Vegas, NV (US)

(73) Assignee: Richard Blankenbecler, Las Vegas, NV (US)

( * ) Notice: Subject to any disclaimer, the term of this patent is extended or adjusted under 35 U.S.C. 154(b) by 887 days.

(21) Appl. No.: 11/912,143

(22) PCT Filed: Apr. 19, 2006

(86) PCT No.: PCT/US2006/014722
§ 371 (c)(1),
(2), (4) Date: Nov. 15, 2007

(87) PCT Pub. No.: WO2006/113794
PCT Pub. Date: Oct. 26, 2006

(65) Prior Publication Data
US 2009/0114846 A1    May 7, 2009

Related U.S. Application Data

(60) Provisional application No. 60/673,050, filed on Apr. 20, 2005, provisional application No. 60/739,708, filed on Nov. 23, 2005.

(51) Int. Cl.
*A61N 5/00* (2006.01)
(52) U.S. Cl. ........................................................ 600/1
(58) Field of Classification Search .................. 600/1–8; 128/897–898
See application file for complete search history.

(56) References Cited

U.S. PATENT DOCUMENTS

| 2001/0039259 A1* | 11/2001 | Korkut | 514/2 |
| 2005/0222250 A1* | 10/2005 | Rezvani | 514/461 |
| 2006/0013801 A1* | 1/2006 | Okunieff et al. | 424/85.2 |

* cited by examiner

*Primary Examiner* — John P Lacyk
(74) *Attorney, Agent, or Firm* — Greenblum & Bernstein, PLC (57) ABSTRACT

This invention describes the use of a process for treating neoplastic masses, in which the damage to healthy cells surrounding the mass is reduced as compared to current treatment processes, hi embodiments, computer programs are used to prescribe a timed treatment sequence to mitigate some of the deleterious effects of cancer radiation treatment or chemotherapy. By initiating natural cell repair mechanisms with an application of a low dose of radiation to healthy tissue prior to the full cancer treatment, the post-treatment damage to the healthy cells can be reduced.

35 Claims, 5 Drawing Sheets

Figure 1
Rotating high dose irradiation of localized cancer.

Figure 2
Rotating low dose irradiation outside of localized cancer.

Figure 3
Low dose irradiation using rotating source
and collimators

Figure 4
Low dose irradiation using source at two angles differing by 90 degrees Figure 5
High Dose Rate (HDR) Brachytherapy Capsule ( ● ) high dose irradiation source for localized cancer where:
A = outline of patient.
B = outline of cancer with capsule implanted.

COMPUTER PRESCRIBED TREATMENT TO REDUCED DAMAGE FROM RADIATION THERAPY AND CHEMOTHERAPY

CROSS-REFERENCE TO RELATED APPLICATIONS

The present application relies on and claims the benefit of the filing date of U.S. Provisional Patent Application No. 60/673,050, filed 20 Apr. 2005, and U.S. Provisional Patent Application No. 60/739,708, filed 23 Nov. 2005, the entire disclosures of both of which are hereby incorporated in their entireties by reference.

BACKGROUND OF THE INVENTION

1. Field of the Invention

The present invention relates to the field of treatment of neoplastic diseases and uncontrolled cell growth. More specifically, it relates to a method for pre-treating the surrounding tissue of a neoplastic growth with a low dosage of radiation before treating the neoplastic growth with a high dosage of radiation or chemotherapeutic agent.

2. Description of Related Art

Neoplastic diseases, or cancers, develop when cells do not respond normally to growth regulation signals. Consequently, some or all of their descendants may proliferate inappropriately to produce tumors. Neoplasias that invade surrounding tissues and ultimately spread throughout the body are called malignant neoplasms or cancers.

Numerous ways of treating neoplastic diseases have been developed over the years. The most widely used localized approaches, surgical removal of cancerous tissues and treatment with ionizing radiation, require a precise knowledge of the location and extent of the cancer. The treatment of choice is typically surgery to remove the tumor because this type of treatment shows a high rate of success and is minimally damaging to unaffected cells of the body. However, in many cases, surgery is not feasible or does not remove all the cancer cells, and therefore, ionizing radiation (radiotherapy) is used instead of or in addition to surgery. High dose radiotherapy results in irreparable damage to cells, for example to their DNA. Cells that enter the next cell cycle may be unable to complete mitosis and die. Those that can complete mitosis may have become cancerous.

For many years, one standard treatment for localized cancer has been to expose the cancerous cells to a lethal dose of radiation. The most common radiation treatment of a deep cancer involves the application of a large dose of x-rays to the cancerous tissues to kill the affected cells. The radiation is applied in a variety of ways engineered to minimize the radiation dose to the surrounding healthy tissue. Two of the commonly used methods involve: 1) the rotation of the x-ray beam around the patient and the cancerous tissues; and 2) the implantation of encapsulated radioactive material or a miniature x-ray source in the cancerous region. Other devices attach the radiation source, a small accelerator or a radionuclide, on the end of a robotic arm, which can be programmed to move around the patient and to aim the radiation beam as programmed.

All of these methods and their implementation are designed to minimize the radiation exposure of the surrounding healthy cells. This mediation can only be partly successful, however. Considerable damage is routinely done to healthy tissue. A sufficiently high dose will certainly kill the cancerous cells. However, the healthy cells surrounding the cancerous tissue will also inevitably suffer damage. The subsequent effects can be very serious for the patient, involving declining health and extreme discomfort. The parameters of the high dose treatment process, such as location, rotation, beam cross-section, and dose are conventionally computed by a computer program, which is typically included as part of the device that supplies the radiation treatment itself. Computer programs and suitable machines to run them and provide radiation therapy are known in the art and widely available commercially.

In a relatively new method of treating using irradiation of cancer tissue, called brachytherapy, the implantation procedure and machines involves inserting, for example, radioactive iridium wires, into the cancer through hollow plastic needles that are placed under ultrasound guidance. Once the desired radiation dose is delivered, the radioactive wires are withdrawn. One specific example of this procedure is referred to as High-Dose Rate (HDR) brachytherapy. This procedure is described in, for example, Theodororescu, D. and Krupski, T. L., "Prostate Cancer: Brachytherapy (Radioactive Seed Implantation Therapy)", Mar. 10, 2005, available at www.e-medicine.com/med/topic3147.htm.

The goal of cancer therapy generally is to remove all cancer cells because a single cancer cell left unimpeded can multiply to ultimately kill the patient. Therefore, when using radiotherapy, it is important that the irradiated site includes all of the cancer. In doing so, it is often the case that surrounding, healthy tissue is irradiated with a damaging or lethal dose. A major problem in the field of radiation therapy is how to avoid harm to the normal cells surrounding a tumor while giving a lethal dose of radiation to the tumor cells.

Radiation oncology research to understand the maximum and thus acceptable levels of radiation exposure to workers has shown that low doses of radiation can induce effects in cells that are different from high doses. For example, while high doses are generally detrimental to cells, low doses can cause cells to become hyper-radiosensitive (HRS) or can induce radio-resistance (IRR). Which response will occur appears to depend on many factors, including the amount of dose given, the type of radiation used, the cell line examined, and the number of and time between doses.

Researchers have examined the phenomenon of hyper-radiosensitivity in mammalian cells to determine if pre-irradiation of cancer cells with a low dose will increase the effect of a subsequent high dose. For example, the effect of low dose pre-irradiation followed by a high dose of radiation was found to accelerate the process of apoptosis or cell death in human leukemic MOLT-4 cells (Chen Z, et al., "Enhancement of radiation-induced apoptosis by preirradiation with low-dose X-rays in human leukemia MOLT-4 cells", *J Radiat Res* 45(2): 239-43, 2004). Other studies have found this response does not occur (Ohnishi T, et al., "Low-dose-rate radiation attenuates the response of the tumor suppressor TP53", *Radiat Res* 151(3): 368-72, 1999).

After examining recent data on the exposure of mammalian cell cultures to very low doses of gamma radiation, it appeared to researchers that low doses of gamma, beta and x-rays were turning on some type of protective process that not only repaired damaged cells but also led to the selective removal of "bad" cells (neoplastically transformed, i.e., possibly cancerous, cells) from the cell community studied. Now, a generally accepted theory behind the phenomenon of induced radio-resistance is that low doses of radiation stimulate production of DNA repair enzymes. The cells, when pre-irradiated with a low dose, are more resistant to a subsequent higher dose because the increased production of repair enzymes has a protective effect.

In this regard, see the review by A. L. Brooks (Brooks, A. L., "Developing a scientific basis for radiation risk estimates: Goal of the DOE Low Dose Radiation Research Program", *Health Physics* 85: 85-102 (2003)). There is a also compendium of papers entitled "Low Dose Radiation Research" that can be found at http://lowdose.tricity.wsu.edu/, and an article by A. Heller (A review of the Low-Dose Radiation research being performed at the Lawrence Livermore National Laboratory can be found in: A. Heller, "Cells Respond Uniquely to Low-Dose Ionizing Radiation", Science and Technology Review, pp. 12-19, July-August 2003; available online at http://www.llnl.gov//str/JulAug03/pdfs/07 03.2.pdf). The precise data in this reference utilizes microarray genome chip methods to measure which particular genes are modulated by a low dose of radiation and which are modulated by a high dose. From this experiment it is now known that a low dose of radiation modulates genes whose functions are to repair cell damage from various causes. These genes have been individually identified. A large dose of radiation modulates a very different, almost orthogonal, set of genes. It is also known that one effect of a low dose is to increase the time to the next cell division (mitosis), thereby allowing more time for the repair to be successfully completed. It is further known that each cell type has a somewhat different protective reaction to low doses of radiation.

For example, pre-irradiation of Swiss albino mice and subsequent irradiation with a high dose resulted in a significant increase in survival of mice compared to the controls (Tiku A B, et al., "Adaptive response and split-dose effect of radiation on the survival of mice", *J. Biosci* 29(1): 111-117, 2004). Furthermore, for example, Cohen et al have suggested that a low dose of radiation may even be protective against cancer (Cohen, B. L., "Cancer risk from low-level radiation", *AJR Am J Roentgenol* 179(5): 1137-1143, 2002).

In addition, a study involving pre-irradiation of a human bladder epithelium cell line and a human bladder carcinoma cell line found that the normal cell line showed induced radio-resistance whereas the carcinoma line showed hyper-radiosensitivity (Schaffer M, et al., "Adaptive doses of irradiation-an approach to a new therapy concept for bladder cancer", *Radiat Environ Biophys* 43: 271-276, 2004). The authors suggest that a novel radiotherapeutic regimen could be developed to enhance the destruction of the tumor while simultaneously protecting normal tissues. However, they do not suggest a specific regimen that could be followed.

Because cell damage caused by radiation, including damage as a result of oxidative stress and DNA breaks, which is termed neoplastic transformation, is an early step in developing cancer, having damaged cells selectively removed from the irradiated population should lead to a reduction, rather than an increase, in the risk of cancer. There is ongoing research on the various mechanisms that could be involved in the selective repair/removal of dangerous cells. For a discussion of the Linear No Threshold hypothesis, or LNT, for estimating damage from radiation exposure, see the review article by Cohen (B. L. Cohen, "Cancer Risk from Low-Level Radiation", *American Journal of Roentgenology* 179: 1137-1143 (2002)).

Mathematical models that are based on known biological mechanisms have been developed that attempt to explain the response of cells to low radiation exposure. This involves cell repair and the selective removal of existing dangerous cells, as well as the induction of new mutants and transformed cells.

It has been suggested that a low radiation dose applied globally to both the healthy and the cancerous regions will induce the protective mechanism and lead to a more effective cancer therapy. However, under this suggestion, the cancer cells as well as the healthy cells would be irradiated (J. Harney, S. C. Short, N. Shah, M. Joiner and M. I. Saunders "Low Dose Hyper-sensitivity in Metastatic Tumors", *Int. J. Rad. Onc. Biol. Phys.* 59: 1190-1195 (2004)). Hence, the defense mechanisms of the cancerous cells will also be turned on, leading to little if any net beneficial effect. Indeed, it would then require even more radiation to kill the cancer cells.

It has also been experimentally verified that a low radiation dose will reduce the damage from a second high radiation dose if there is a suitable time delay between the exposures. An example of one particular type of data is a study of the effect of time and dose modulated radiation on the lifetime and malignant cell transformation of mice (R. E. J. Mitchel, "Radiation Biology of Low Doses", *International Zeitschrift fur Kernenergie*, 47: 28-30 (2002)). Similar experiments by the same group have involved a second exposure to chemical carcinogens rather than a large radiation dose. It was found that low doses of in vivo beta-irradiation of mouse skin applied 24 hours prior to treatment with a DNA damaging chemical carcinogen reduced tumor frequency by about 5-fold.

In this regard, a cell that has turned on its repair mechanisms communicates chemically with its neighbors. This is called the "bystander effect". The neighboring cells then respond by turning on their own repair mechanisms, even though they have not received a lethal dose of a harmful agent or energy. All forms of radiation are expected to initiate the same or similar repair mechanisms. See, for example, Ko, S. J. et al., "Neoplastic transformation In Vitro after exposure to low doses of mammographic-energy X rays: Quantitative and mechanistic aspects", *Radiation Research* 162: 646-654 (2004), and B. R. Scott, "A biological-based model that links genomic instability, bystander, and adaptive response", *Mutation Research* 568: 129-143 (2004).

In summary, there is strong evidence that very low doses of x-ray, beta, and gamma radiation (from less than 0.01 Gy up to about 0.1 Gy=10 rads) turn on processes that, given sufficient time to be fully activated, can repair subsequent severe cellular damage. This damage can be from a large radiation dose or from a chemical carcinogen, and if the cell is irreparable, preferentially induces apoptosis (cell death). However, the art has not recognized a suitable way to take advantage of this effect. Accordingly, there is still a need in the art for a way to protect normal tissue surrounding a tumor while giving a lethal dose of radiation to the tumor itself.

SUMMARY OF THE INVENTION

The present invention addresses this need in the art by providing a method for protecting normal, healthy cells surrounding a tumor or other neoplastic growth in a subject's body. As a general matter, the method induces a protective response in the healthy cells by exposing them to low doses of radiation, then exposes the neoplastic cells to harmful doses of radiation or other cell-damaging energy or chemicals. By inducing the protective response in the surrounding healthy cells, the invention improves the survival of these healthy cells upon receiving the harmful level of radiation or other cell-damaging energy or of one or more chemotherapeutic substance that the healthy cells are inevitably exposed to during conventional treatment of the neoplastic cells.

In a first aspect, the invention provides a method of protecting at least one non-neoplastic cell of a subject currently or previously suffering from a neoplastic disease from the harmful effects of radiation or chemotherapeutic agents used to treat the disease. In general, the method comprises: 1) exposing the subject, and in particular at least one non-neoplastic cell that is sensitive to damage by radiation or at least one chemotherapeutic agent, to a pre-determined low dose of radiation, while, at the same time, not exposing one or more target neoplastic cells to the low dose of radiation; 2) waiting a pre-defined period of time that is between about one hour and about 24 hours; and 3) exposing both the sensitive non-neoplastic cell or cells and the target neoplastic cell or cells to a cell-damaging dose of radiation or a cell-damaging dose of one or more chemotherapeutic agents. According to the method, the first step of exposing results in protection of the non-neoplastic cell or cells from the harmful effects of the subsequent dose of radiation or chemotherapeutic agent or agents. Of course, other steps may be included in the method, including before the first exposing, between any of the three recited steps, or after the second exposing step. Those of skill in the art are well aware of suitable additional steps that may be included in the method, and can include them without any undue or excessive experimentation. For example, the method can be implemented to treat a patient after a neoplastic mass has been removed by surgery, to treat the site of growth of the mass to ensure that any remaining neoplastic cells are killed. In embodiments, the method includes intentionally or unintentionally avoiding treating non-neoplastic cells in the vicinity of the neoplastic mass. It is often preferably to kill some healthy cells than allow neoplastic cells to escape a treatment regimen unkilled.

In another aspect, the invention provides a method of treating at least one neoplastic cell with a harmful amount of radiation or a harmful amount of a physical substance. The method generally comprises: 1) exposing at least one non-neoplastic cell that is in contact with, or in the physical vicinity of, at least one neoplastic cell to a dose of radiation effective to induce a protective response in the non-neoplastic cell(s); and 2) exposing the neoplastic cell(s) to a harmful amount of energy or at least one substance; where exposing the neoplastic cell(s) to the harmful amount of energy or substance(s) has a greater harmful effect on the neoplastic cell(s) than on a non-neoplastic cell that was exposed to the protective response-inducing dose of radiation.

In general, the method of the invention can be practiced in vivo as a therapeutic method of treating a neoplastic disease. Likewise, it can be practiced in vitro as part of a screening method for effective new chemotherapeutic agents for use in conjunction with radiation therapy. Accordingly, the invention provides for the use of a two-step treatment procedure to treat neoplastic cells in vivo and/or in vitro, use of machines that provide radiation therapy for neoplastic diseases to practice the present method, and use of chemotherapeutic agents as part of the present method. For in vitro uses of the method, the method typically comprises: exposing at least one healthy, non-neoplastic cell of a known cell type to a low dose of radiation; waiting 1 hour to 24 hours; exposing the cell to a cell-damaging level of radiation or at least one chemotherapeutic agent; and determining the effect of the cell-damaging radiation or chemotherapeutic agent on the healthy, non-neoplastic cell. According to this aspect of the method, the protective effect of the low level of radiation on the healthy cell can be determined by the ultimate effect of the cell damaging radiation or chemotherapeutic agent. The in vitro method may also be used to determine the effect of various radiation levels on protection of cells, and to determine the protective effect of various low level radiation doses to various high level radiation doses or various chemotherapeutic agents. This information can be used to select various chemotherapeutic agents to be used against particular neoplasias (e.g., cell types that are neoplastic) and to determine appropriate combinations of low dose, high dose, and chemotherapeutic agents for use in treating a particular neoplastic disease.

In yet another aspect, the invention provides a method of protecting subjects that are to be exposed to high doses of radiation, such as workers who are scheduled to enter a high radiation area for inspection, maintenance, or clean-up. In general, the method comprises reducing the cell death of healthy cells in a subject exposed to elevated levels of radiation, where the elevated levels are levels above levels accepted as safe, but lower than amounts known to cause immediate (within days) cell death. The method comprises exposing the subject to a low dose of radiation, which is sufficient to activate cell protective mechanisms; waiting 1 to 24 hours; and exposing the subject to elevated levels of radiation. According to the method, the initial exposure to low dose radiation turns on cellular protective processes that protect the cells of the subject's body when later exposed to elevated levels of radiation.

BRIEF DESCRIPTION OF THE DRAWINGS

The accompanying drawings, which are incorporated in and constitute a part of this specification, illustrate several embodiments of the invention, and together with the written description, serve to explain certain principles of the invention.

DETAILED DESCRIPTION OF VARIOUS EMBODIMENTS OF THE INVENTION

Reference will now be made in detail to various exemplary embodiments of the invention, examples of which are illustrated in the accompanying drawings. The following detailed description is provided to give details on certain embodiments of the invention, and should not be understood as a limitation on the full scope of the invention.

Broadly speaking, the invention provides a method of treating at least one neoplastic cell with a harmful amount of electromagnetic energy (e.g., X- or gamma-radiation) or a harmful amount of a physical substance (e.g., chemotherapeutic agent). The method comprises treating at least some non-neoplastic cells that are susceptible to the effects of harmful amounts of radiation or harmful amounts of chemical agents, such as healthy cells surrounding the neoplastic cell(s), with a non-lethal dose of electromagnetic energy prior to treating the neoplastic cells with a harmful, and preferably fatal, amount of electromagnetic energy and/or a harmful, and preferably fatal, amount of one or more chemical agents. The present invention recognizes for the first time that treatment of healthy cells that are susceptible to the harmful effects of radiation or chemotherapy, such as healthy cells surrounding a neoplastic mass, with a low dose of electromagnetic energy, and in particular radiation, protects them, at least to some extent, from the damaging effects of a later exposure to cell-killing levels of electromagnetic energy or one or more chemotherapeutic agents that are directed at the neoplastic mass, but also come into contact with the healthy, non-neoplastic cells. In many embodiments, the invention uses a low radiation dose applied to carefully chosen regions of a patient's body to suppress the damaging effects from a subsequent cancer treatment that involves either radiation therapy or chemotherapy. The preliminary low dose is directed to those regions of the body that are non-cancerous and that should preferably survive the treatment that is intended to kill or damage the cancerous cells. The cancerous region should ideally receive very little or no radiation during the low dose stage. A low dose of radiation turns on repair mechanisms in the cell, which increases the probability that the cell will survive a later exposure to harmful radiation or chemical treatment. The cancerous tissue, on the other hand, does not receive a first low dose of radiation and is therefore still fully sensitive to either a large radiation dose or to a chemotherapy treatment.

As used herein, the terms neoplastic (and all of its forms), cancer (and all of its forms), and tumor (and all of its form) are used interchangeably to indicate a cell or condition in which there is uncontrolled or abnormally fast growth of one or more cells of a particular cell type. Neoplastic cell growth can occur in vivo to produce a mass of cells within an organism, such as a human, or can occur in vitro to produce a culture of cells that might or might not have characteristics of cell lines. Accordingly, the neoplastic cells can be, but are not necessarily, immortal. Likewise, the cells can be, but are not necessarily, primary cells obtained directly from a cancerous tissue.

Furthermore, as used herein the terms radiation (and all of its forms) and electromagnetic energy are used interchangeably to indicate energy of one or more wavelengths of the electromagnetic spectrum. Particular energy levels (i.e., wavelengths) are known in the art as suitable for treatment of neoplasias by killing of neoplastic cells upon exposure of the cells to the energy. However, the invention is not limited to use of such wavelengths, but instead can be used with any wavelength of the electromagnetic spectrum. For example, the invention contemplates use of a particular wavelength of energy that can activate a substance that can absorb one wavelength of energy and re-emit at another wavelength. For ease of reference, electromagnetic energy is typically referred to herein as radiation, and this term is to be broadly interpreted.

More specifically, radiation is energy that comes from a source and travels through some material or through space. Thus, light, heat, and sound are types of radiation. One useful type of radiation according to the present invention is ionizing radiation, which is radiation that can produce charged particles (i.e., ions) in matter. Ionizing radiation is often produced in the medical setting by man-made devices, such as X-ray machines. It is well known that ionizing radiation can be produced by unstable atoms (i.e., radioactive atoms), which are atoms that have an excess of energy, mass, or both, and which shed or emit that energy and/or mass in the form of radiation in order to achieve a stable state. For the purposes of this invention, it is to be understood that there are two kinds of radiation: electromagnetic (e.g., light, gamma radiation, X-rays) and particulate (e.g., proton or neutron emission, beta and alpha radiation).

It is also to be understood that, where the invention relates to therapeutic treatment of a subject, a diagnosis of a localized cancer has been made and the size, shape, and location of the cancerous mass has been determined by standard methods known in the art. In other words, it is to be understood that the invention relates to in vivo therapy of a patient in need thereof, and the routine procedures for identifying such patients and characterizing their tumor(s) have been performed. By subject, it is meant any living organism in which a neoplasia may exist. Thus, a subject may be, but is not limited to, a human or other animal (e.g., a dog, cat, horse, bird, or other companion or agricultural animal). As used herein, the terms subject, patient, person, and animal, unless otherwise indicated, are used interchangeably to indicate a living organism in which a neoplasia may exist. Accordingly, the present invention has application in both the human health field and in veterinary medicine.

The invention relates to in vivo and in vitro treatment of cells. In aspects relating to in vivo uses, it is generally a method of therapeutic treatment, which can be curative or prophylactic. Thus, the method can be practiced on a subject suffering from a neoplastic disease, such as one in which a neoplastic mass is growing, to reduce the growth of, reduce the size of, or eliminate the neoplastic mass. In addition, the method can be practiced on a subject who previously suffered from a neoplastic disease, such as one who had a neoplastic mass removed by surgery or radiation treatment, to ensure that all neoplastic cells of the mass are killed. Furthermore, the method can be practiced on a subject who is not currently, or was not previously, suffering from a neoplastic disease, but is scheduled to be exposed to a relatively high dose of radiation, such as a person who is scheduled to enter a high radiation zone.

In a first aspect, the invention provides a method of protecting at least one non-neoplastic cell of a subject currently or previously suffering from a neoplastic disease from the harmful effects of radiation or chemotherapeutic agents used to treat the disease. The method is thus a curative or prophylactic therapeutic method. The curative method preferably, but does not necessarily, result in total elimination (i.e., total curing) of the patient suffering from the neoplastic disease; rather, it can result in partial curing by reduction of the growth of one or more neoplastic cells. In general, the method comprises: 1) exposing the subject, and in particular at least one non-neoplastic cell that is sensitive to damage by radiation or at least one chemotherapeutic agent, to a pre-determined low dose of radiation, while, at the same time, not exposing one or more target neoplastic cells to the low dose of radiation; 2) waiting a pre-defined period of time that is between about one hour and about 24 hours; and 3) exposing both the sensitive non-neoplastic cell or cells and the target neoplastic cell or cells to a cell-damaging dose of radiation or a cell-damaging dose of one or more chemotherapeutic agents. According to the method, the first step of exposing results in protection of the non-neoplastic cell or cells from the harmful effects of the subsequent dose of radiation or chemotherapeutic agent or agents.

In another aspect, the method of the invention generally comprises: 1) exposing at least one non-neoplastic cell that is in contact with, or in the physical vicinity of, at least one neoplastic cell to a dose of radiation effective to induce a protective response in the non-neoplastic cell(s); 2) waiting a predetermined amount of time, which is sufficient to permit treated cells to express at least some proteins involved in protecting the cell from damage inflicted by high doses of radiation or high doses of chemotherapeutic agents; and 3) exposing the neoplastic cell(s) to a harmful amount of energy or at least one harmful chemical substance. Typically, the method also comprises exposing at least one of the previously treated cells with the harmful amount of energy or chemical substance. Thus, in its basic form, the invention provides a three-step or three-stage procedure for treating neoplastic cells. Due to the protective effect of the first step on the non-neoplastic cells, in the method, the treatment of non-neoplastic cells with a low dose of radiation is performed prior to treatment of the neoplastic cells and/or non-neoplastic cells with a high dose of radiation or a chemical agent.

According to the invention, exposing the neoplastic cells to the harmful amount of energy or the chemotherapeutic substances has a greater harmful effect on the neoplastic cells than on a non-neoplastic cell that was exposed to the protective response-inducing dose of radiation. Induction of protective mechanisms in the normal, healthy cells surrounding the neoplastic cells (e.g., solid tumor) improves their ability to survive a high dose of radiation or high dose of chemotherapeutic agent that they are later exposed to as a collateral effect of treatment of the neoplastic cells. On the other hand, because the neoplastic cells have not received the protective dose of radiation, they are more sensitive to the high dose of radiation or chemotherapeutic agent, and have a higher rate of cell death as a result of the later treatment step.

In embodiments, the first step of the method of the invention comprises exposing at least one non-neoplastic cell that is sensitive to the high dose of radiation or chemical agent, such as one that is in the physical vicinity of at least one neoplastic cell, to a low dose of radiation. A low dose of radiation is defined as the amount of radiation that causes induced radioresistance (IRk), preferably in the range of about 0.01 to about 1 total Gray units (Gy) or 1 to 100 Rads. In embodiments, the range is from about 0.01 to about 0.5 Gy, from about 0.05 Gy to about 0.1 Gy, from about 0.01 to about 0.1 Gy, and from about 0.05 to about 0.25 Gy. Of course, any particular amount of radiation within these ranges is contemplated by the invention, as is any range within these stated ranges, and one of skill in the art would immediately recognize that all specific amounts and ranges are envisioned by these broadly recited exemplary ranges. The form of radiation therapy used can be any described previously or others. For example, X-rays, targeted radionucleotides, brachytherapy, and neutron capture therapy can be used with this method of invention.

In embodiments, the cells that are treated with a low dose of radiation are those that are in contact with the neoplastic cells or are in the surrounding area. As a general matter, all cells that lie between the radiation source and the tumor and its immediate surroundings are considered cells that are in the surrounding area, and will be exposed to low-dose radiation. This is a necessary result of the fact that the radiation must pass through all tissues of the patient that are present between the radiation source and the tumor. As discussed above, it is now routine to vary the location of the source of radiation during high-dose treatment of tumors, to reduce the total exposure of surrounding cells to cell-damaging radiation. For example, the radiation source is rotated about the patient's body (or vice versa) to continuously deliver radiation directly to the tumor while delivering only short bursts of radiation to any one particular cell of the surrounding tissue. According to the present invention, any of the cells that are to receive high-dose radiation as a result of being in the pathway of the high-dose beam, even for a brief time, for treatment of the neoplastic diseases are considered cells in the surrounding area. The rotation, dosing, etc. for the high-dose treatment will be determined by the practitioner prior to initiating treatment; therefore, the cells in need of treatment with low-dose radiation will be known ahead of time, and the method can account for this information. Thus, where the method is practiced using a second step that involves exposure of neoplastic cells to high-dose radiation, cells that are in contact or in the surrounding area are cells that will be in the pathway of the radiation beam during the high-dose radiation therapy step.

In embodiments, the cells that are treated with a low dose of radiation are those that are physically separated from the neoplastic cell(s) and/or neoplastic mass to be therapeutically treated, but that are sensitive to treatment with radiation or chemotherapeutic agents. It is known that certain cells and cell types are particularly sensitive to radiation or certain chemotherapeutic agents, and that systemic treatment with harmful doses of radiation or chemotherapeutic agents causes these cells to be killed at a high rate. Thus, in certain embodiments of the invention, these sensitive cells are treated with a low dose of radiation prior to treatment of the subject with harmful amounts of radiation and/or chemotherapeutic agents.

As discussed above, where the method is practiced using a step that involves exposure of one or more neoplastic cells to a harmful level of radiation, cells that are treated beforehand with a low level of radiation are typically those that are in the radiation pathway during exposure of the neoplastic cell(s) to a high level of radiation. While it is envisioned that these cells may be anywhere within the body of the subject, they are typically within 10 centimeters of the neoplastic cell(s), or within the distance between the surface of the subject's body and the neoplastic cell(s).

Where the method is practiced using a step that involves exposure of neoplastic cells to one or more chemotherapeutic agents, cells that are in contact or in the surrounding area are those that are in physical contact with one or more neoplastic cells or are within about 10 cm of a neoplastic cell. To avoid unnecessary exposure of cells to radiation, in some embodiments, the cells are within about 5 cm, about 4 cm, about 3 cm, about 2 cm, or about 1 cm from the neoplastic cells. Due to the precise nature of control of radiation therapy now possible through the use of computers to control pathways of irradiation, it is possible to achieve a highly concentrated, well defined radiation beam for treatment of subjects. Therefore, the low-dose treatment may be exquisitely controlled to provide treatment of only those cells likely to need it, thus minimizing peripheral damage to cells that need not be exposed to the high-level radiation.

It is to be noted that, in this document, all values given, unless specifically noted, are intended to include a margin of error of 10% about the recited value. Thus, a value of 10 should be understood, unless recited as "precisely" or another similar word, to mean "about 10" or anywhere from 9 to 11. In some embodiments, the value is to be understood to include a margin of error of 5%, 2%, or 1%. While not recited specifically with each number or range discussed herein, it is to be understood that each value is contemplated as including any of these error ranges. Where not specified, each value is to be understood to inherently include a 10% error range.

Control of delivery of the low dose of radiation within the context of treatment with chemotherapeutic agents is particularly relevant where the chemotherapeutic agent will be delivered to the neoplastic cells in a targeted manner. For example, where the chemotherapeutic agent will be delivered directly to a neoplastic mass by injection, implantation, etc., pre-treatment of surrounding tissues can be particularly important seeing that the agent will be present in the neoplastic tissue and might diffuse outwardly into healthy tissue surrounding the neoplastic tissue. Likewise, where a chemotherapeutic agent is delivered systemically, but is capable of preferentially targeting to the neoplastic cells (e.g., an immunotoxin or immunoconjugate), it can be important to treat surrounding cells to protect them from diffusion of the toxin, etc. from the neoplastic tissue after delivery of it by way of the antibody. Furthermore, where systemic treatment with chemotherapeutic agent(s) is used, it can be important to radioprotect some sensitive cells, tissues, and/or organs at a distant site from the tumor, and it can be important to specifically irradiate those sensitive cells, tissues, and/or organs without irradiating other surrounding cells or cell types.

As mentioned before, computers may now be used to exquisitely control the location and level of radiation exposure to a patient's tissues. This fact is relied upon in embodiments of the present invention to permit fine control of which cells receive low levels (protective) radiation. One general benefit of the present invention is to minimize the number of cells surrounding a neoplastic mass that are damaged or killed by radiation therapy. To achieve the highest benefit, pre-treatment with low levels of radiation should be accomplished on as many cells as possible, without pre-treatment of any neoplastic cells. Use of computers to monitor and deliver treatment permits the practitioner to protect essentially all healthy cells surrounding a neoplastic mass. Of course, while it is generally beneficial to protect as many healthy cells as possible, it might often be desirable to avoid low-dose treatment of cells in direct or very close (e.g., 5-10 cell diameters) contact with the neoplastic cells to ensure that no neoplastic cells are given a protective dose of radiation. That is, in some situations, the practitioner may find that it is more beneficial to the patient to expose some healthy cells to high dose radiation (or chemotherapeutic agents) without prior treatment with a protective dose of radiation, rather than risk protecting some neoplastic cells with a low dose of radiation. Those of skill in the art may select which cells are to receive the low dose of radiation and which are not, and such a selection is well within the level of skill of those practitioners.

In embodiments, computers are used to design a dosing regimen for delivery of low level radiation to protect healthy, non-neoplastic cells. In other embodiments, computers are used to design a dosing regimen for delivery of high level radiation to neoplastic cells and the previously protected healthy, non-neoplastic cells. Thus, in some implementations of the method, a computer is used to design a dosing regimen for delivery of both low level and high level radiation. The method can include controlling by computer the radiation dose for low level irradiation, high level irradiation, or both.

In embodiments, the therapeutic method of the invention comprises exposing the neoplastic cell(s) to a harmful amount of energy or at least one substance, in an amount that causes harm to at least one neoplastic cell. The harmful amount of energy can be delivered in any of the forms of radiation therapy described previously, such as, but not necessarily limited to, X-ray, targeted radionucleotides, brachytherapy, and neutron capture therapy or other forms of delivery. The amount of harmful energy can be 8 Gy (800 Rads) or higher. For example, it may be precisely or about 10 Gy, precisely or about 15 Gy, precisely or about 20 Gy, precisely or about 25 Gy, precisely or about 30 Gy, precisely or about 35 Gy, precisely or about 40 Gy, precisely or about 45 Gy, precisely or about 50 Gy, precisely or about 55 Gy, precisely or about 60 Gy, precisely or about 70 Gy, or more. In general, it is within the range of about 8 Gy to about 70 Gy. Of course, it may be any specific number within this range, and one of skill in the art may envision each particular amount without the need for each to be specifically recited herein.

Alternatively, the second step of exposing can comprise exposing at least one neoplastic cell to at least one chemotherapeutic agent, which may vary depending on the kind of tumor targeted, patient history, etc. For example, gastric cancer chemotherapy can involve 5-fluorouracil, platinum compounds, taxanes, and irinotecan. Breast cancer therapy can use trastuzumab, bevacizumab, and taxanes. Non-small cell lung cancer chemotherapy can involve platinum compounds, taxanes, gemcitabine, vinorelbine, and/or irinotecan. While not so limited, chemotherapy for prostate cancer can primarily employ one or more taxanes. Those of skill in the art are well aware of the numerous chemotherapeutic agents available to treat various cancers, and may select one or more that are deemed appropriate, without any undue or excessive experimentation.

According to the invention, exposing, in the context of radiation, comprises directing electromagnetic radiation toward a cell such that it strikes the cell or a cell component, or passes through the cell. It is to be understood that certain types of radiation according to the invention are generally considered to comprise energy rather than matter, and thus is often not considered as "contacting" a cell. However, according to the present invention, the term "contacting" includes passing energy or mass through a cell, whether the energy or mass actually impinges upon a physical component of the cell or passes through the cell without having any effect. It is to be understood that such energy or mass may pass through many cells without having any effect or may pass through many cells without having any effect while ultimately having an effect on a cell.

On the other hand, exposing, in the context of one or more chemotherapeutic agents, comprises causing the agent(s) or their metabolic products to physically contact one or more cell and, preferably, enter the cell. Thus, exposing may comprise administering an agent to a patient via any route, including, but not limited to, injection, infusion, inhalation, transdermal, transmucosal, intraperitoneal, intramuscular, sublingual, rectal, vaginal, oral, and the like. Those of skill in the art are well aware of the various ways that chemotherapeutic agents can be administered to a patient, and any such way may be used according to the invention. Exposing may thus include administering, dosing, delivering, or otherwise giving the agent to a patient. Exposing may also comprising administering the agent(s) systemically or directly to a site of interest, such as a neoplastic mass. In other embodiments, exposing comprises contacting the cell(s) with the agent(s) by introducing the agent(s) and cell(s) into the same environment, such as in an animal tumor model or an in vitro assay medium.

There is a time period between the first exposing step and the second exposing step. Thus, while it should be evident from the general language of the method, the method comprises waiting a pre-determined amount of time between the first exposing and the second exposing steps. This time delay is provided to allow the healthy cells that have been treated with the low dose of radiation to develop a protective response. As should be understood, the protective response is due to biochemical changes in the cells. It thus requires induction of expression of certain proteins and/or repression of expression of others. Such a process requires time, not only for new protein synthesis to occur in the cell, but for removal of other proteins, and for the new proteins to become active or perform the function(s) that result in protection of the cell. Studies have shown that the protective response is developed in mammalian cells in about 1 to about 24 hours. When given less time, the response is either undeveloped or incompletely developed, and the cells show significant cell damage upon subsequent treatment with high doses of radiation. When much more than 24 hours is provided between low dose and high dose treatments, the cells likewise show a reduction in survival, ostensibly due to a return of the cells to a normal state (i.e., the protective response being turned off). While a protective response is still seen when the time delay is less than 1 hour or more than 24 hours, it is preferred according to the method that the two treating steps be performed between about 1 and about 24 hours apart. For example, they can be performed about or exactly 1 hour apart, about or exactly 2 hours apart, about or exactly 3 hours apart, about or exactly 4 hours apart, about or exactly 5 hours apart, about or exactly 6 hours apart, about or exactly 7 hours apart, about or exactly 8 hours apart, about or exactly 9 hours apart, about or exactly 10 hours apart, about or exactly 15 hours apart, about or exactly 20 hours apart, or about or exactly 24 hours apart. In embodiments, the time is more than 24 hours, such as 28 hours, 30 hours, 36 hours, 42 hours, 48 hours, or more. Of course, any particular amount of time within these ranges, including portions of hours, can be used according to the invention—one of skill in the art will immediately recognize all of the particular, specific amounts of hours and minutes encompassed by these exemplary numbers, and may select any particular amount of time without it needing to be specifically identified in this document.

The method of the invention can be a method of treating a neoplastic cell. It can also be a method of treating a healthy, non-neoplastic cell in the vicinity of a neoplastic cell or that are highly sensitive to radiation or cell-damaging chemical agents, where the treatment protects the healthy cell from later exposure to a harmful level of radiation or chemicals. The method, at its core, comprises a three-step process in which healthy cells are first treated with low levels of radiation to induce a protective response, followed by treatment of both the neoplastic cells and the healthy cells with cell-damaging, and preferably cell-killing, levels of radiation or chemicals after waiting for cellular protective mechanisms to be expressed. The method results in killing of a higher percentage of the neoplastic cells than the surrounding healthy cells or sensitive healthy cells. It thus is a method of protecting the healthy cells from the deleterious effects of the high levels of radiation and/or chemicals in the second treatment step.

As a method of treatment, the method is designed to achieve a detectable change in a cell. The change may be any change that is deemed desirable by the practitioner, and should be a change that is detectable within a reasonable amount of time (e.g., about one year or less). As the method relates in general to treatment of neoplastic cells, the effect is often an effect on growth of a cell. For example, where the effect relates to a neoplastic cell, the effect may be slowing of growth of a cell or cell mass. It may also be complete cessation of growth of the cell or mass. Preferably it is a reduction in the viability of the cell or mass, for example by killing of the cell or killing of many cells of the mass such that the mass is reduced in size. In some embodiments, the treating results in killing of a neoplastic cell, and/or killing of some or all of the neoplastic cells of a tumor.

On the other hand, in the context of treatment of healthy cells, the method can achieve a detectable change that is an improvement in the survivability of the cell. The treatment may thus result in induction of expression of one or more proteins in the cell that protect, at least to some extent, the cell from the harmful effects of radiation or certain chemicals. It may also result in survival of the cell when exposed to radiation or chemicals, where the cell would otherwise die from such exposure.

The method can be practiced in vivo as a therapeutic method of treating a neoplastic disease. It thus may be a method of treating a subject suffering from a neoplastic disease. It is, in embodiments, a method of treating a subject suffering from a tumor or cancer, such as a solid tumor. The type of tumor is not limited within the context of the invention, and thus may be, without limitation, lung cancer, breast cancer, prostate cancer, liver cancer, brain cancer, kidney cancer, bone cancer, esophageal or mouth cancer, colon cancer, a cancer of the gastrointestinal tract, bladder cancer, or any type of skin cancer. The cancer may be at any stage in development, and may be metastatic or confined.

Alternatively, the method may be a prophylactic method that treats subjects that are to be exposed to moderately high levels of radiation. There are many workers throughout the world who are, in the process of their employment or by accident, exposed to moderately high levels of radiation. Such workers include those at military sites, nuclear processing sites, nuclear testing sites, or at nuclear power generating sites. Such workers may, at times, be exposed to a full year's or more of recommended total radiation dose, which is a high level, but significantly less than the high levels used in conventional treatment of neoplastic masses. According to the present invention, the method may include prophylactic treatment of such workers to protect them from the radiation that they are to be exposed to. In embodiments, the method is a method of protecting radiation workers from exposure to moderate levels of radiation. By moderate levels, it is to be understood that, while the actual amount of radiation in the area in which the worker will be present may be extremely high, the total time of exposure may be low, such that the total radiation received will be moderate. In embodiments, the method is a method of increasing the amount of radiation a subject can be exposed to over a given period of time, such as over a one day, two day, one week, or one year period. The method can be a method of increasing the maximum allowable radiation to a human for a given period of time, such as for one year or two years.

One advantage that can be achieved by embodiments of the invention is that a practitioner, such as a medical doctor or other qualified person, can deliver a higher dose of radiation to a patient than possible with present treatment methods. The dose may be broken into multiple irradiation sessions, if desired, including one or more low-dose irradiation treatments. Because the low dose radiation turns on protective mechanisms in treated cells, they can withstand higher doses of harmful radiation. Accordingly, neoplastic cells may be treated with higher levels of radiation without an increase in damage or potential damage to healthy cells. Thus, either the total radiation dose may be lowered while still achieving the same neoplastic cell killing effect, or the total radiation dose to neoplastic cells may be increased without increasing the damage to healthy cells. In embodiments, the treatment is divided into numerous bursts of radiation, resulting in a total irradiation of neoplastic cells that is high. For example, radiation doses can be administered several hours apart, for example multiple times at 2 hour intervals, 4 hour intervals, or the like. Thus, in embodiments, the therapeutic method is a method of increasing the dose of radiation to a cancer, with an increased probability of killing cancerous cells but without an increased probability of harming or killing healthy cells.

The method of the invention may be performed multiple times on a single subject. For example, it is well known that solid tumors often require multiple treatments with high doses of radiation to reduce and ultimately destroy the tumor. The present invention contemplates repeating the method two or more times, at two or more different times, to achieve an overall treatment regimen that achieves a desired goal. As alluded to above, many goals may be envisioned by the practitioner, including, but not necessarily limited to, killing at least one neoplastic cell, reducing the increase in size of a tumor over time, reducing the size of a tumor over time, and eliminating a tumor from a subject's body. In certain embodiments, the goal is to reduce the size of, or completely eliminate, a solid tumor. In embodiments, this goal or any other goal is achieved while permitting a high percentage of healthy cells surrounding the tumor to survive (where a high percentage is defined as a percentage that is higher than would be achieved without giving the cells a protective dose of radiation).

The method may also be practiced as part of a more complex treatment regimen, such as is known in the art. That is, depending on the type and extent of development of a cancer, a patient may be treated with any number of different treatment regimens, which are implemented by his attending physician based on any number of considerations. The present invention may be practiced as a part of any such regimens, as deemed useful by the practitioner. Accordingly, the method of the invention may further comprise performing surgery on the patient, treatment with a number of chemotherapeutic agents, repetition of one or more steps, and the like. Those of skill in the medical arts may devise such treatment regimens without undue or excessive experimentation. Furthermore, all of the various permutations of treatment regimens need not be detailed here for those of skill in the art to recognize suitable procedures and techniques that may be combined to provide a successful treatment.

The method may be practiced in vitro on cells grown in culture. When practiced in vitro, it may be a method for identifying parameters that are useful in in vivo treatment regimens. Thus, an in vitro screening method may comprise the treatment method of the present invention. The screening method may be designed to identify effective new chemotherapeutic agents for use alone or in conjunction with radiation therapy.

In general, the in vitro method comprises exposing at least one non-neoplastic cell to an amount of radiation that induces a protective response in the cell, where the protective response is one that protects the cell from damage caused by a later exposure to radiation or chemical treatment. Typically, the method further comprises a second treating step in which the cells are treated with high-dose radiation or a chemical (e.g., chemotherapeutic agent), preferably a lethal amount, and observed for the effect of that radiation or chemical on the cell. The two treating steps are separated by a pre-determined amount of time, such as from 1 to 24 hours. The results of practice of the method in vitro can provide useful information for selection of radiation types and levels of exposures, and can also provide useful information for selection of chemical agents that can be advantageously used in conjunction with low level radioprotective dosing of healthy cells.

As should be evident, the invention provides for the use of a treatment procedure to treat neoplastic cells in vivo and/or in vitro. In some embodiments, the use includes use of two doses of radiation, the first dose being a low dose delivered to surrounding healthy cells or cells sensitive to high levels of radiation or chemotherapeutic agents, but not the neoplastic cells, to induce a protective response, and the second dose being a high dose delivered to both the neoplastic cells and the previously treated healthy cells. Use of the treatment procedure results in increased damage, and preferably killing, of the neoplastic cells as compared to the healthy cells, the difference being a result of, at least in part, the first dose of radiation to the healthy cells. In other embodiments, the use includes use of one dose of radiation followed by a dose of at least one chemical agent that harms cells. The dose of radiation is a low dose delivered to healthy cells, but not the neoplastic cells, to induce a protective response in those cells.

The dose of chemical(s) provides a sufficient amount of at least one chemical to the neoplastic cells to cause a decrease in cell growth. Preferably, the dose is sufficient to cause the cell to cease growing, and more preferably, to die. Use of the treatment procedure results in increased damage, and preferably killing, of the neoplastic cells as compared to the healthy cells, the difference being a result of, at least in part, the first dose of radiation to the healthy cells.

The invention also provides for the use of a treatment procedure to treat a patient suffering from a neoplastic disease, such as a solid tumor. The use of the procedure follows the general guidelines discussed above. Preferably, the use results in a slowing in the growth of the tumor. More preferably, the use results in a cessation of the growth of the tumor. In some embodiments, the use results in shrinkage of the size of the tumor as a result of cell death of tumor cells. It is to be understood that in some embodiments, the tumor is destroyed, ablated, removed, etc. by the use of the method.

The invention further provides for the use of machines that provide radiation therapy for neoplastic diseases to practice the present method. Use of the machines, optionally with chemotherapeutic agent(s), provides for therapeutic treatment of a patient suffering from a neoplastic disease. In accordance with the discussion above, use of a machine to provide radiation therapy according to the invention can result in slowing of cell or tumor growth, cessation of cell or tumor growth, neoplastic cell death, tumor shrinkage, and/or tumor removal, ablation, destruction, etc.

In addition, the invention provides for use of chemotherapeutic agents as part of a treatment procedure to treat a patient suffering from a neoplastic disease. Use of one or more chemotherapeutic agents to treat a patient suffering from a neoplastic disease can provide any and all of the results discussed above.

One aspect of the invention is the use of computers and computer programs to treat neoplastic disorders. Computers are now widely used to calculate doses of radiation to be administered to patients, and to target those doses to particular tissues. The present invention contemplates the use of one or more computers to design the delivery of low doses of radiation to tissues and cells surrounding a neoplastic mass or to other healthy cells, but not the neoplastic mass itself. In embodiments, it further contemplates use of one or more computers to design the delivery of a high dose, preferably a cell-killing dose, of radiation to at least one cell of the neoplastic mass.

EXAMPLES

The invention will now be described in more detail with reference to certain non-limiting examples of practice of the method of the invention. The following Examples are presented to provide details on certain embodiments or features of embodiments of the general method of the invention, and are not to be understood as limiting the invention in any way.

While not wishing to be held to any one particular explanation for its effectiveness, the invention, in embodiments, can be thought to rely on two basic elements. First, the use of computers to optimize the radiation exposure by controlling the position, spatial distribution, and intensity of the x-ray radiation source. Second, the recently discovered and unexpected effect of radiation on cells—namely that a low radiation exposure followed later by a high dose is less damaging to a cell than the total of the two exposures applied with no delay. As discussed earlier, this is commonly interpreted by assuming that the low dose of radiation initiates repair mechanisms in the cell. These repair mechanisms increase in effectiveness for a period of time and then eventually decay and return to their steady state values.

It has been estimated that the repair mechanisms in some human cells require about 6 hours to become fully active and might start to decay after about 24 or more hours. There is some evidence that the lifetime of the repair mechanism increases as the dose rate decreases at the same total dose; to keep the same total low dose the exposure time should be increased.

In conventional radiation therapy, it is standard practice to fractionate the full required dose into several sessions spread over several days. It is also quite common to hyper-fractionate the sessions into several each day, in which the sessions are repeated over several days. Before an optimum treatment schedule can be designed using the present invention, which in embodiments utilizes a low dose followed by a later high dose, or alternatively a low dose followed by multiple high doses, the time dependence of the repair mechanisms should be measured with sufficient accuracy. If this information is known, the radiation treatments can be interleaved with the proper time gaps for maximum protective effect. As a general rule, each tumor and patient will require optimization; however, the general guidelines presented herein allow for effective treatment even if not optimized for a particular tumor and patient.

Thus if a large dose of radiation is applied while the repair mechanism is at or near its full strength, the patient has a better chance to repair/replace and mitigate any serious damage to his irradiated healthy cells. There is some evidence that a low dose preceding a high dose by the proper amount of time, at least 6 hours or so, will reduce the probability that a cancer will be induced in the irradiated cells when compared to the two doses being applied with zero time delay. There is further independent evidence that a preliminary low radiation dose can also turn on cell repair mechanisms that can improve cell survivability under chemical attack, such as experienced during a standard chemotherapy treatment. Thus, the treatment procedure discussed in this document is useful in chemotherapy as well as in radiation therapy.

One purpose of this disclosure is to describe the use of computer programs to tailor the application of x-rays to minimize damage to healthy cells while ensuring severe, desirably fatal, damage to the cancerous cells. If the dose applied to the cancer is fixed at the standard present value, the treatment method of this invention can lead to a small increase in total radiation dose to healthy tissue, but with reduced total damage. Alternatively, this procedure can be used to increase the radiation dose to the cancerous cells, thereby increasing lethality while keeping the damage to healthy tissue at the standard (presumably acceptable) present value.

Figure 1:
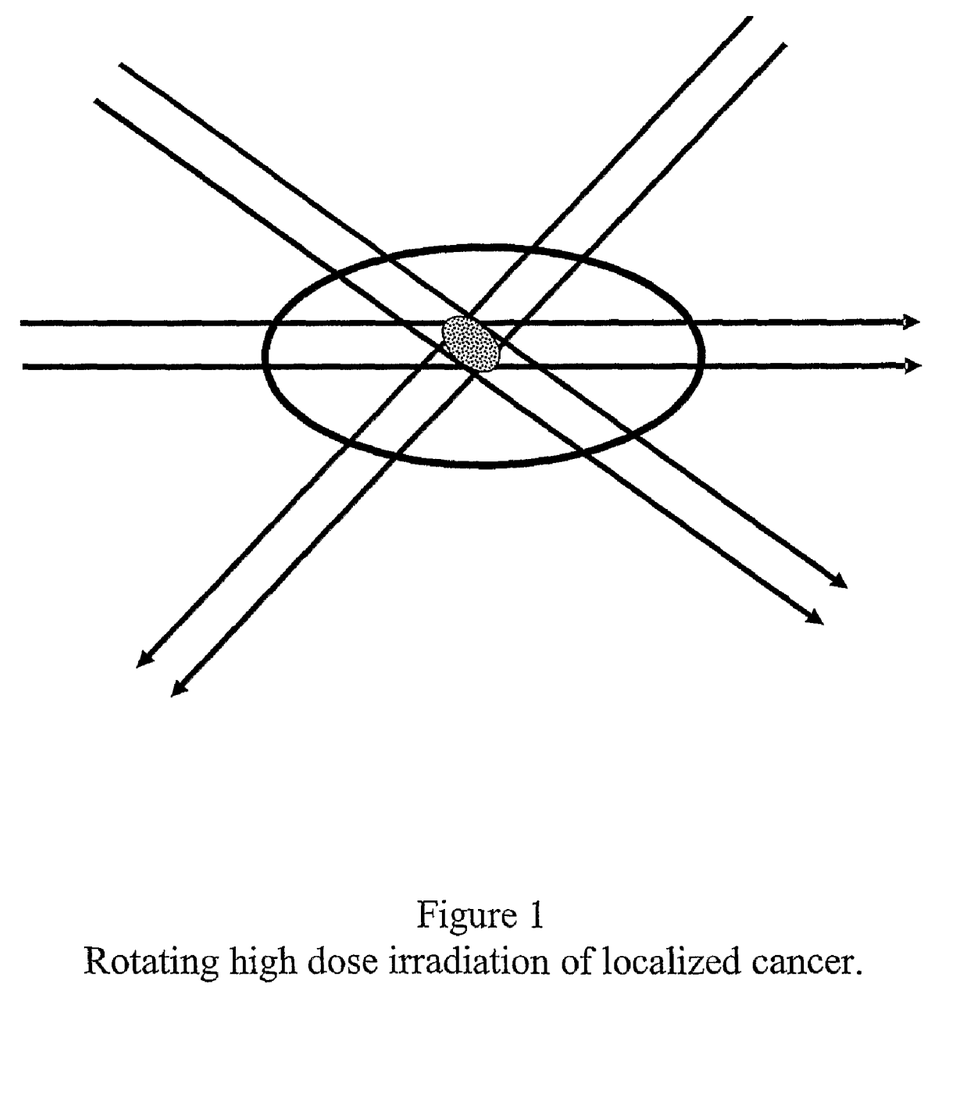
FIG. 1 is a cross-sectional schematic diagram of current conventional radiation therapy of a neoplastic tissue mass in a subject.

The first step in the application of an embodiment of this invention is to compute the radiation dose throughout the patient for the selected mode of the high dose treatment. The rotation of the radiation source and its beam cross-section or the location and lifetime of implantation of the radioactive source is determined by a computer program so that the maximum dose, eventually a lethal dose, is delivered into the cancerous mass, but with as small a dose as possible delivered to the surrounding healthy tissue. This procedure is referred to herein as MAXRAD. This step is illustrated in FIG. 1, in which a rotating radiation beam centered at the cancerous mass is depicted, or in FIG. 5 which depicts an implanted radioactive source. These are examples of the present standard cancer treatment procedures.

In embodiments, the second step is to determine the parameters of the low dose stage of the treatment. The radiation source and beam direction parameters are chosen so that a minimum dose is delivered to the cancerous mass. The optimum beam delivery occurs when the cancerous mass receives a zero dose of radiation. This procedure is referred to herein as MINRAD. Again, the radiation dose throughout the patient is computed. This computer program is somewhat different from that in the first stage. It can be realized using a variety of mathematical algorithms. The program can use many of the mathematical techniques used in the first step but with a different objective, namely the minimization of the dose in the cancerous mass rather than the maximization of the dose.

Figure 2:
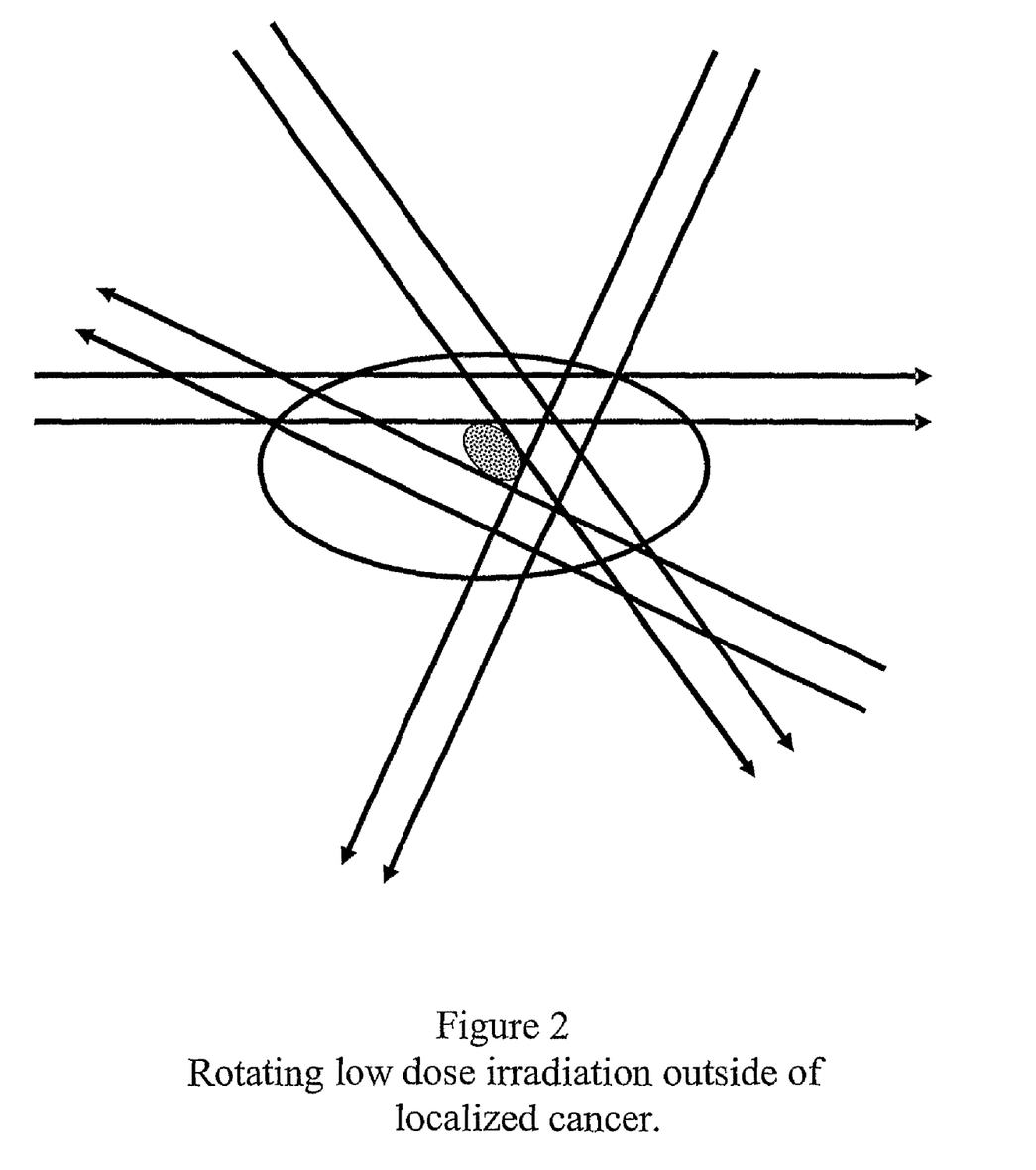
FIG. 2 is a cross-sectional schematic diagram of treatment of non-neoplastic cells of the current invention.

One way of physically implementing this step is illustrated in FIG. 2, in which a rotating radiation beam is shown that avoids the cancerous mass and instead irradiates the healthy tissues outside the cancer. This step is also illustrated in FIG. 6.

Figure 3:
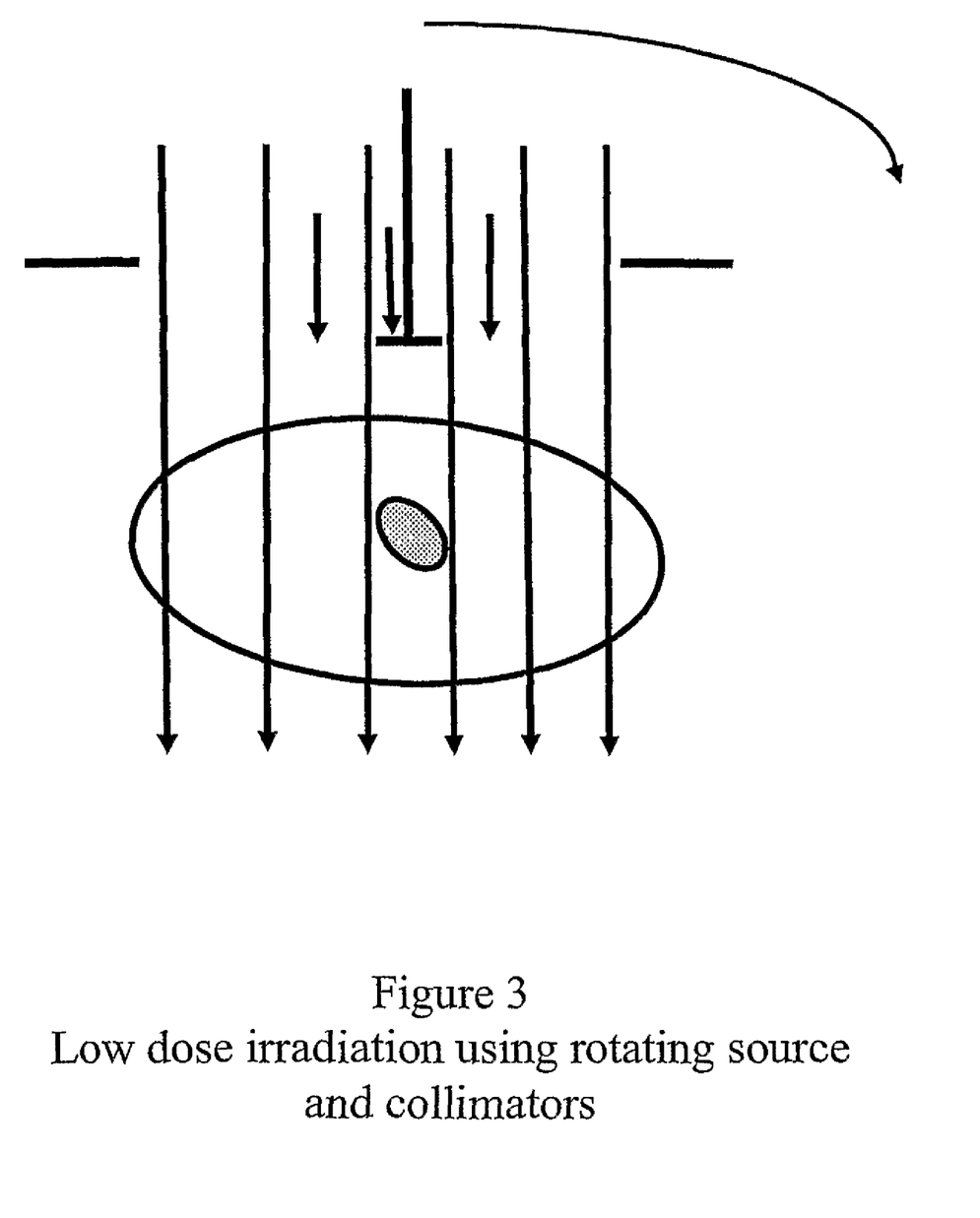
FIG. 3 is a cross-sectional schematic diagram of treatment of non-neoplastic cells surrounding a neoplastic mass, where a rotating source with collimator is used to block irradiation of the neoplastic cells.
Figure 4:
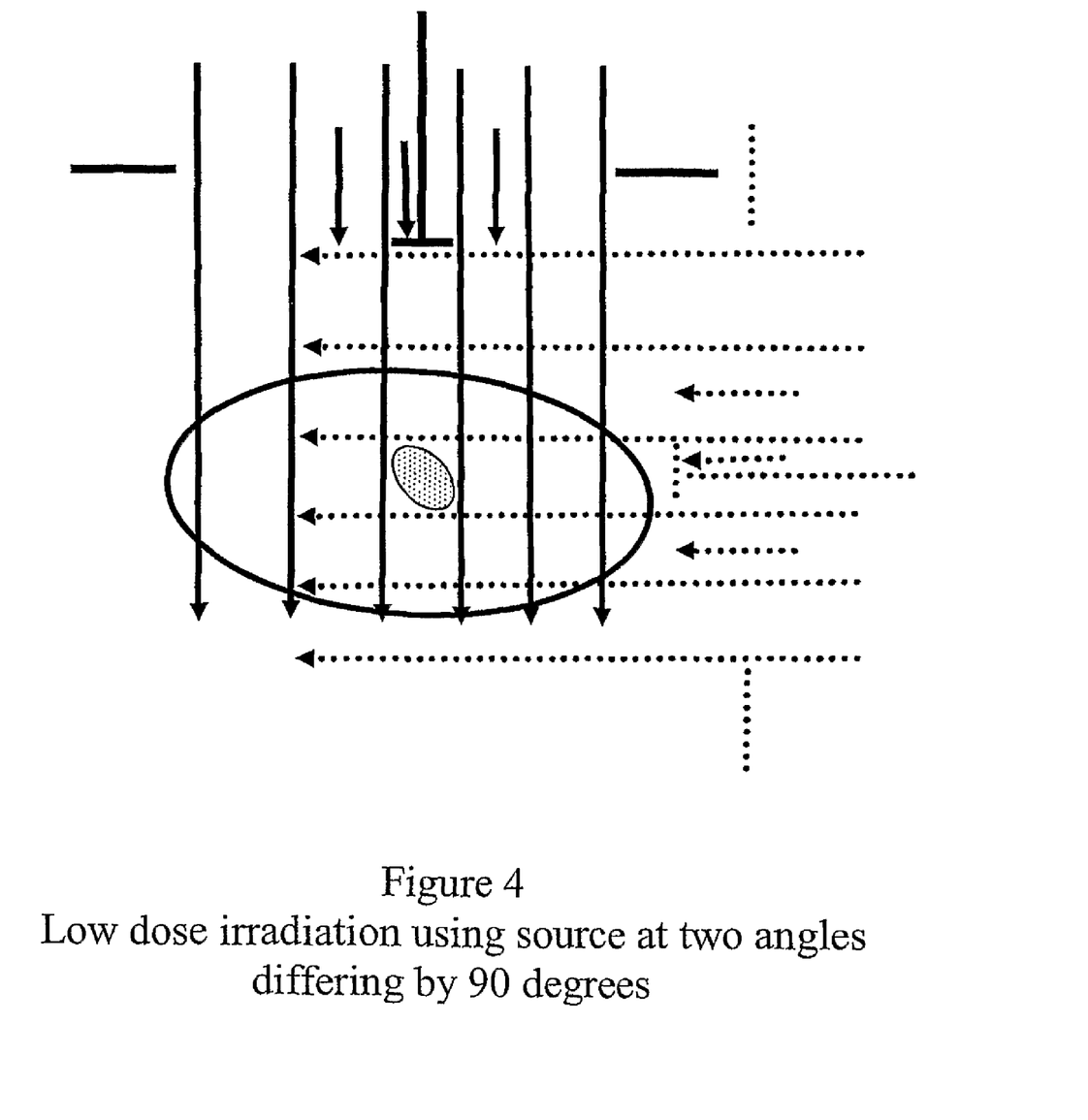
FIG. 4 is a cross-sectional schematic diagram of treatment of non-neoplastic cells surrounding a neoplastic mass, where the source and collimators are not continuously rotating but are set at two angles separated by 90 degrees; the irradiation of the neoplastic cells is blocked.

In FIG. 3, a rotating beam source is illustrated that uses a beam collimator, or block, that prevents any radiation from reaching the cancer. In FIG. 4, the beam is fixed at only two angles, separated by 90 degrees.

In embodiments, the third step is the treatment itself. To do so, one will first run MINRAD at a low dose that is sufficient to trigger the cell repair mechanism. This step is schematically shown in FIG. 2. After waiting for the time period required to develop the optimum cell repair mechanism, the MAXRAD treatment is run. Recall that there will be less radiation to the surrounding tissues because of the rotation and movement of the beam of radiation. This step is schematically shown in FIG. 1, and in FIG. 5 for an implanted source. It should be noted that the cancerous mass forms a three dimensional object so that the computer programs need to take this into account. The figures show only a two dimensional cross-section of the physical layout.

Where an optimal dose has been calculated, then the second step listed can be practiced to provide the optimum results. In this case, the computer program used in step 2 determines the radiation source, rotation, intensity and beam cross section so that by delivering, as close as possible, the optimum repair dose to the cells damaged by the high intensity radiation procedure described in the first step.

It should be noted that the total radiation dose to the healthy cells, the MIN-RAD dose plus the MAXRAD dose, need not exceed the standard dose presently administered for cancer treatment. The second MAXRAD dose can be reduced slightly so that the total of the radiation dose to the healthy cells can be the standard dose. Therefore, it should be clear that this treatment choice need not pose any increased risk to the healthy cells of the patient when compared to the standard treatment. However, if the MAXRAD dose is fixed at the standard value, then the additional MINRAD dose will result in an small increase of radiation to the healthy cells, but with reduced overall damage.

Note that the low dose preconditioning need not be from the same source as the high dose. A standard X-ray source can be used for this irradiation if its beam can be arranged suitably and if it can supply the required (low) dose. There is some evidence that it may be beneficial to have the pretreatment applied at a very slow dose rate over a time period that is sufficient to deliver the required total low dose.

In the application to ameliorate the side effects of chemotherapy treatment, there is a minor increase in risk from the low dose of radiation. The cost/benefit ratio of the additional radiation must be carefully evaluated as well as which healthy organs or tissues to irradiate. Often, these will be selected healthy tissues that are most susceptible to damage by the chemotherapy treatment and hence need protection.

At this point, a more detailed geometric description of the Figures and the method will be provided. In FIG. 1, the cancerous mass is at the center of a circle which defines the path of the radiation source. The beam of radiation is aimed parallel to the radius, pointing directly at the center. The mass receives radiation from every point on the periphery and the cells away from the center receive correspondingly less radiation dose. The longitudinal coordinate, perpendicular to the plane of the figure, should also be mapped by the computer program in the same manner as described above. It should be noted that these are cross-section, two-dimensional figures.

In FIG. 2, the beam of radiation is aimed at an angle to the radius such that with the given width of the beam, the central mass receives no radiation. If the central mass is not circular, the angle can be varied as the source moves around the circle to ensure that there is no radiation passing through the cancer. Instead of aiming the beam at a finite offset angle, the source can be displaced laterally from its axis of rotation to achieve the same result.

In FIG. 3, the cancerous mass is at the center of a circle which defines the path of the radioactive source. The beam of radiation is collimated, and there is an absorbing mask to insure that the central (cancerous) mass receives no radiation. The radiation source rotates around the cancerous site. In FIG. 4, the setup is as described in FIG. 3. However, in this case, the radiation source is placed at only two points separated by 90 degrees around the circle. The irradiation dosage is not as smooth as that given as in FIG. 3, but if the required pre-dose value has a large acceptable limit, this simpler procedure may be sufficient.

Figure 5:
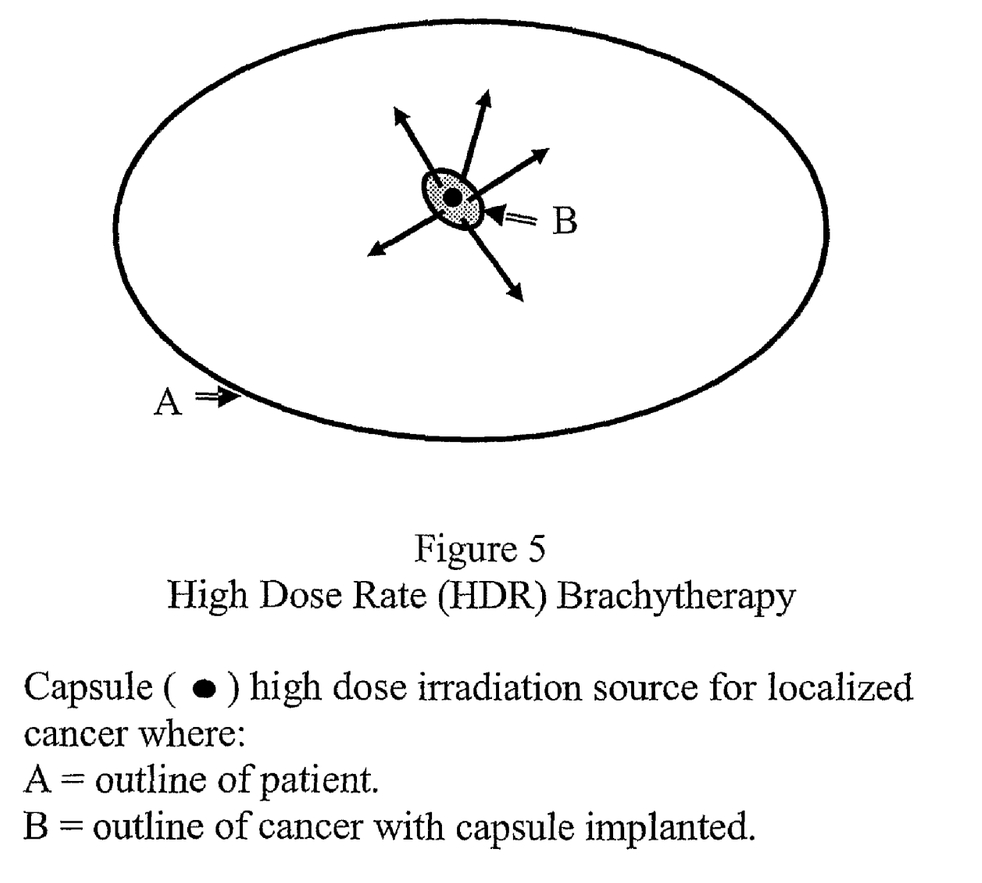
FIG. 5 is a cross-sectional schematic diagram of brachytherapy according to the present invention.

In FIG. 5, a radioactive source is implanted in the cancerous mass for a given amount of time and then removed after delivering the desired large radiation dose. The radiation spreads out radially from the source, dying off as roughly as $1/r^2$ where r is the distance from the source. Thus, the further a cell is from the source capsule, the less radiation it receives.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated by the following claims.

The invention claimed is:

1. A method of protecting at least one non-neoplastic cell of a subject currently or previously suffering from a neoplastic disease from the harmful effects of radiation or chemotherapeutic agents used to treat the disease, said method comprising:
   exposing at least one non-neoplastic cell of the subject that is sensitive to damage by radiation or at least one chemotherapeutic agent to a pre-determined low dose of radiation;
      wherein said exposing does not comprise exposing at least one target neoplastic cells or target non-neoplastic cell to the low dose of radiation;
   waiting a pre-defined period of time that is between about one hour and about 48 hours; and
   exposing both the sensitive non-neoplastic cell or cells and the target cell or cells to a cell-damaging dose of radiation or a cell-damaging dose of one or more chemotherapeutic agents;
   wherein the first exposing results in protection of the non-neoplastic cell or cells from the harmful effects of the subsequent dose of radiation or chemotherapeutic agent or agents.

2. The method of claim 1, wherein the cell that is sensitive to damage by radiation or at least one chemotherapeutic agent is in contact with or in close proximity to a target neoplastic cell of the neoplastic disease.

3. The method of claim 1, wherein the cell that is sensitive to damage by radiation or at least one chemotherapeutic agent is located at a site that is distant from a site where a target neoplastic cell is located.

4. The method of claim 1, wherein the non-neoplastic cell or cells are exposed to a low level of ionizing radiation.

5. The method of claim 1, wherein the non-neoplastic cell or cells are exposed to about 0.01 Gray Units (Gy) to about 1 Gy of ionizing radiation.

6. The method of claim 1, wherein exposing the non-neoplastic cell or cells comprises exposing them to ionizing radiation, and wherein the method further comprises: blocking radiation exposure of one or more target neoplastic cells with a collimator.

7. The method of claim 1, wherein the pre-determined amount of time of waiting is between about 1 hour and about 10 hours.

8. The method of claim 1, wherein the pre-determined amount of time of waiting is between about 1 hour and about 6 hours.

9. The method of claim 1, wherein the pre-determined amount of time of waiting is between about 3 hours and about 6 hours.

10. The method of claim 1, wherein the step of exposing both sensitive non-neoplastic cells and target neoplastic cells comprises exposing the cells to cell damaging levels of ionizing radiation.

11. The method of claim 10, wherein the level of ionizing radiation is between about 5 Gy and about 70 Gy.

12. The method of claim 10, wherein the level of ionizing radiation is between about 5 Gy and about 30 Gy.

13. The method of claim 1, wherein the step of exposing both sensitive non-neoplastic cells and target neoplastic cells comprises exposing the cells to cell damaging levels of one or more chemotherapeutic agents.

14. The method of claim 1, which is a method of therapeutic treatment of cancer with radiation.

15. The method of claim 1, which is a method of therapeutic treatment of cancer with chemotherapy.

16. The method of claim 1, wherein the subject is a human.

17. The method of claim 1, wherein the subject is an animal.

18. The method of claim 1, wherein both steps of exposing comprise exposing the subject to ionizing radiation, and where the location and amount of each radiation dose is controlled by a computer.

19. The method of claim 1, further comprising
   performing surgery to remove a neoplastic mass comprising at least one target neoplastic cell prior to the first exposing step,
      wherein the first exposing step comprises exposing some, but not all, non-neoplastic cells originally surrounding the neoplastic mass to a low dose of radiation, and
      wherein the second exposing step comprises exposing all non-neoplastic cells originally surrounding the neoplastic mass to a high dose of radiation.

20. A method of treating a subject having a neoplastic mass within its body, said method comprising:
   irradiating healthy cells surrounding the neoplastic mass with a low dose of radiation, wherein the dose is sufficient to induce a protective response in the healthy cells, but not sufficient to kill the cells, and wherein cells of the neoplastic mass are not irradiated;

waiting a pre-determined amount of time; and treating cells of the neoplastic mass with a harmful amount of radiation or a harmful amount of a chemical agent.

21. The method of claim 20, wherein the method results in higher survival rate of the healthy cells as compared to equivalent healthy cells that are not irradiated with the low dose of radiation.

22. The method of claim 20, wherein the neoplastic mass is a solid tumor.

23. The method of claim 20, wherein the low dose is 0.01 Gy to 1 Gy.

24. The method of claim 20, wherein the harmful amount of radiation is 5 to 80 Gy.

25. The method of claim 20, wherein waiting comprises waiting 1 to 48 hours between the irradiating step and the treating step.

26. The method of claim 20, wherein the subject is a human.

27. The method of claim 20, wherein the subject is an animal.

28. The method of claim 20, wherein the radiation dose is controlled by a computer.

29. A method of reducing healthy cell killing during a method of treating a neoplastic growth in a patient, said method comprising:

exposing to a low dose of radiation healthy cells that are sensitive to cell killing by cell damaging levels of radiation or cell damaging levels of a chemotherapeutic agent;

wherein the low dose is sufficient to induce a protective response in the cell, but not sufficient to kill the cell, and wherein cells of the neoplastic growth are not irradiated;

waiting a pre-determined period of time; and treating cells of the neoplastic growth with a harmful amount of radiation or a harmful amount of a chemotherapeutic agent.

30. A computer-implemented therapeutic treatment of a neoplastic mass in a subject's body, said method comprising:

using a computer to calculate the amount and location of radiation to be delivered to healthy cells surrounding a neoplastic mass;

exposing the healthy cells, but not neoplastic cells of the neoplastic mass, to a low dose of radiation;

using a computer to calculate the amount and location of radiation to be delivered to neoplastic cells of the neoplastic mass; and exposing the neoplastic cells to a high dose of radiation.

31. The method of claim 30, wherein exposing of the neoplastic cells to a high dose of radiation comprises exposing the healthy cells to a high dose as well.

32. An in vitro method of screening for chemotherapeutic agents that are effective in treating a neoplastic growth, said method comprising:

exposing at least one healthy, non-neoplastic cell of a known cell type to a low dose of radiation, wherein the dose is sufficient to induce a radioprotective response in the cell(s);

waiting 1 hour to 24 hours;

exposing the cell(s) to a cell-damaging level of at least one chemotherapeutic agent; and determining the effect of the chemotherapeutic agent on the healthy, non-neoplastic cell, wherein an improvement in survival of the healthy cell indicates suitability of the chemotherapeutic agent in a method of treating a neoplastic growth.

33. The method of claim 32, further comprising comparing the effect of the chemotherapeutic agent on neoplastic cells of the cell type of a neoplastic growth of interest.

34. A method of prophylactic treatment of a subject who is to be exposed to moderately high levels of radiation, said method comprising:

exposing the subject, or a portion of the subject's body, to a low dose of radiation, wherein the dose is sufficient to induce a radioprotective effect in cells of the subject;

waiting a predetermined amount of time; and exposing the subject to moderately high levels of radiation;

wherein exposing the subject to a low dose of radiation results in a reduction of damage to the subject by the moderately high level of radiation, as compared to another subject exposed to the same amount of radiation, but without an initial low dose exposure.

35. The method of claim 34, wherein the subject is a worker in a nuclear facility.

* * * * *